(12) United States Patent
Gering

(10) Patent No.: US 7,693,349 B2
(45) Date of Patent: Apr. 6, 2010

(54) SYSTEMS AND METHODS FOR INTERACTIVE IMAGE REGISTRATION

(75) Inventor: David T Gering, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 904 days.

(21) Appl. No.: 11/464,808

(22) Filed: Aug. 15, 2006

(65) Prior Publication Data

US 2008/0044104 A1    Feb. 21, 2008

(51) Int. Cl.
*G06K 9/32* (2006.01)

(52) U.S. Cl. .................. 382/294; 382/282; 382/307

(58) Field of Classification Search .......... 382/282, 382/294, 307
See application file for complete search history.

(56) References Cited

U.S. PATENT DOCUMENTS

| | | | | |
|---|---|---|---|---|
| 6,640,145 | B2 * | 10/2003 | Hoffberg et al. | 700/83 |
| 6,850,252 | B1 * | 2/2005 | Hoffberg | 715/716 |
| 6,930,707 | B2 * | 8/2005 | Bates et al. | 348/78 |
| 7,006,881 | B1 * | 2/2006 | Hoffberg et al. | 700/83 |
| 7,379,627 | B2 * | 5/2008 | Li et al. | 382/305 |

OTHER PUBLICATIONS

D.T. Gering, A. Nabavi, R. Kikinis, N. Hata, L.J. O'Donnell, W.E.L. Grimson, F.A. Jolesz, P.M. Black, W.M. Wells. "An integrated visualization system for surgical planning and guidance using image fusion and an open MR". JMRI 2000; 13:967-975, retrieved from Internet on Aug. 17, 2007.

S. Haker, S. Angenent, A. Tannenbaum, R. Kikinis, G. Sapiro, M. Halle. "Conformal Surface Parameterization for Texture Mapping". IEEE Transactions on Visualization and Computer Graphics Apr.-Jun. 2000, retrieved from Internet on Aug. 17, 2007.

S.T. Roweis, L.K. Saul. "Nonlinear Dimensionality Reduction by Locally Linear Embedding". Science Dec. 2000; 290:2323-2326, retrieved from Internet on Aug. 17, 2007.

Lawrence K Saul and S.T. Roweis, Introduction to Locally Linear Embedding.   http://www.cs.toronto.edu/~roweis/lle/publications. html, retrieved from Internet on Aug. 17, 2007, retrieved from Internet on Aug. 17, 2007.

J.B. Tenenbaum, V.d.Silva, J.C. Langford. "A Global Geometric Framework for Nonlinear Dimensionality Reduction". Science Dec. 2000; 290:2319-2323, retrieved from Internet on Aug. 17, 2007.

(Continued)

*Primary Examiner*—Yosef Kassa
(74) *Attorney, Agent, or Firm*—Dean D. Small; Small Patent Law Group

(57) ABSTRACT

System and method for incorporating user input on the fly during an otherwise automatic registration process. During rigid registration, user input adjusts the current computed pose or transformation that relates the two images being aligned. During warping, user input adjusts the flow field locally, and is gradually smoothed into the surrounding flow field. During multi-scale registration where images are first aligned at a course resolution, and subsequently at progressively finer resolutions, user input is applied at the current scale. User input is detected during the automated process either by interrupts or polling. Between user inputs the registration results are re-rendered.

20 Claims, 12 Drawing Sheets

OTHER PUBLICATIONS

T.P. Thirion. "Image matching as a diffusion process: an analogy with Maxwell's demons". Medical Image Analysis 1998; 2, retrieved from Internet on Aug. 17, 2007.

P. Viola, W.M. Wells. "Alignment by maximization of mutual information". International Journal of Computer Vision Sep. 1997; 24:137-154, retrieved from Internet on Aug. 17, 2007.

W.M. Wells, P. Viola, H. Atsumi, S. Nakajima, R. Kikinis. "Multi-modal volume registration by maximization of mutual information". Medical Image Analysis 1996, retrieved from Internet on Aug. 17, 2007.

A.J. Yezzi, J.L. Prince. "A PDE Approach for Measuring Tissue Thickness". In: Computer Vision and Pattern Recognition (CVPR). Kauai, Hawaii: 1998; 87-92, retrieved from Internet on Aug. 17, 2007.

3D Slicer. http://www.slicer.org, retrieved from the Internet on Aug. 17, 2007.

A.V. Bartroli, R. Wegenkittl, A. Konig, E. Groller, E. Sorantin. "Virtual Colon Flattening". In: VisSym 2001. 2001; 127-136, retrieved from the Internet on Jan. 23, 2007.

\* cited by examiner

SYSTEMS AND METHODS FOR INTERACTIVE IMAGE REGISTRATION

FIELD OF THE INVENTION

This invention relates generally to the field of digital image processing, and in particular to image registration.

BACKGROUND OF THE INVENTION

Image registration is the act of spatially mapping the coordinate system of one image to the coordinate system of another image. Registration techniques, for example, can be useful in medical procedures in which a pre-operative image space needs to be properly correlated to a real-time physical space.

Automatic registration algorithms generally consist of three components: A similarity metric for measuring the correspondence between the images (e.g.: cross correlation, mutual information; A set of allowable transformations that can be applied to one image in order to match it to the other (e.g.: rigid, affine, free-form); and. A method for searching the space of allowable transformations to find the optimal transform as the solution (e.g.: gradient descent, stochastic gradient descent, Powell's method, least squares).

Automatic registration methods perform adequately in well-posed cases, but these methods experience difficulty in routine clinical use. Challenges are introduced by pathology, imaging artifacts, and differences in image acquisition.

Rigid registration methods find a correspondence between two images by seeking to maximize a similarity metric computed globally (over a large span of the image, if not its entirety). These global measures encounter difficulty in clinical settings when the field of view of one image does not encompass the entire field of view of the other. This challenge is more pronounced when the similarity metric is mutual information (useful for registering T1-weighted MRI to T2-weighted MRI, or MRI to CT), as opposed to correlation. In these cases, correspondence can be accurately computed locally, but the global discrepancies cause greedy search algorithms to converge to local minima. The search algorithms in medical applications are typically greedy, referring to the method of searching a solution space by following gradient descent, or a similar deviant such as stochastic gradient descent. The reason for this is that the images are very large, and the applications must meet stringent clinical demands for speed.

Non-rigid registration methods typically begin with a rigid or affine registration step, followed by a more refined registration that corrects local misalignments. The localized warping attempts to align the anatomical structures, but there exists ambiguity between whether an observed intensity difference between images is caused by a difference in positioning of anatomy, or other factors. These other factors include imaging artifacts, contrast uptake, and pathology.

For the reasons stated above, and for other reasons stated below which will become apparent to those skilled in the art upon reading and understanding the present specification, there is a need in the art for an automatic registration method that overcomes the shortcomings of the prior art. There is also a need for improved registration that allows the user of an automatic registration system to input information during the registration process.

BRIEF DESCRIPTION OF THE INVENTION

The above-mentioned shortcomings, disadvantages and problems are addressed herein, which will be understood by reading and studying the following specification.

In accordance with a first aspect of the present invention, computerized method for image registration by accessing a set of images to be registered through an automatic registration process, selecting an automatic registration process, applying the selected automatic registration process on the acquired set of images, receiving user input, incorporating the received user input into the current stage of the application of the selected registration process on the acquired set of images, and repeating the action of receiving and incorporating until the registration of the acquired set of images is within a predetermined condition.

The set of images can be one or more MRI image, CT image, pathology image, image with artifacts, X-ray image, ultrasound image, region of interest image.

The automatic registration process is one of rigid registration, warping registration, a combination of rigid and non-rigid registration, multi-scale registration, similarity registration, localized correlation or localized mutual information registration.

The user input is one or more global control, localized control, pasting.

The global control is applied to a selected image, the localized control is applied to a region of a selected image, and the pasting is when the user aligns images that are tiled with very little overlap.

The user input is one or more of translation factor, rotation factor, scaling factor, region of interest factor, and flow vectors.

The displaying of image registration progress is through one or more of side-by-side comparison, blended overlay, side-by-side comparison and blended overlay, and user defined information.

The displaying of graphical cues from received user inputs is through one or more of drawing lines, arrows, and shading on the images.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into sections. A system level overview is described, methods or particular implementations of embodiments are described, and the hardware and the operating environment in conjunction with which embodiments may be practiced are described. Finally, a conclusion of the detailed description is provided.

System Level Overview

Figure 1:
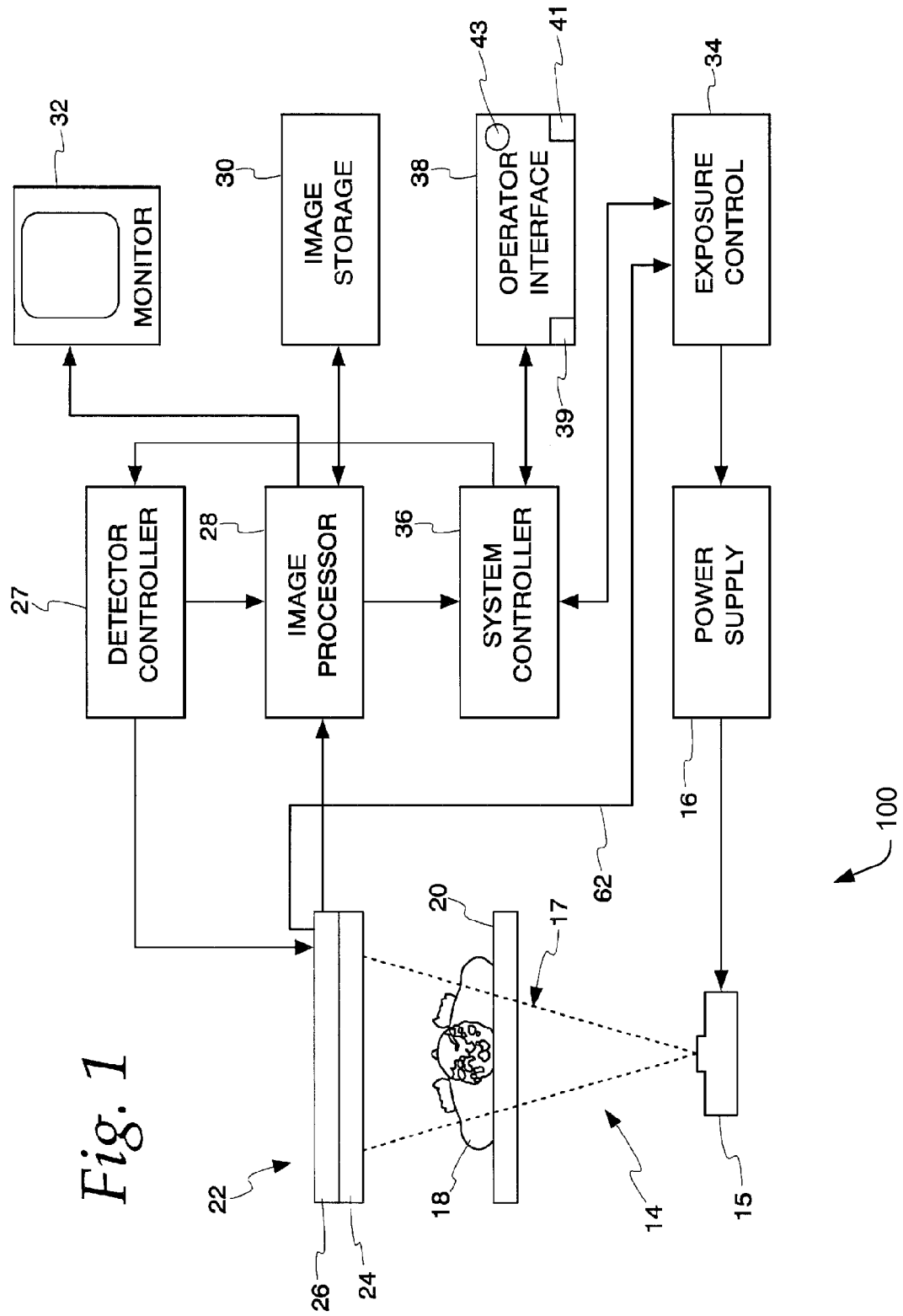
FIG. 1 is a diagram illustrating a system-level overview of an embodiment.

FIG. 1 is a block diagram that provides a system level overview of an imaging system 100. Embodiments are described as operating in a multi-processing, multi-threaded operating environment on a computer, such as computer 202 in FIG. 2.

FIG. 1, an X-ray system 100 includes an X-ray tube 15 or X-ray source 15 which, when excited by a power supply 16, emits an X-ray beam 17. As illustrated, the X-ray beam is directed toward a patient 18 lying on an X-ray transmitting table 20. The portion of the beam, which is transmitted through the table and the patient, impinges upon an X-ray detector assembly 22. The X-ray detector assembly 22 comprises a scintillator 24 that converts the X-ray photons to lower energy photons in the visible spectrum. Contiguous with the scintillator 24 is an image photo detector array 26, which converts the light photons into an electrical signal. A detector controller 27 contains electronics for operating the detector array 26 to acquire an image and to read out the signal from each photo detector element.

The output signal from the image photo detector array 26 is coupled to an image processor 28 that includes circuitry for collecting, processing, and enhancing the X-ray image signal. The processed image is displayed on a video monitor 32 and may be stored in an image storage device 30. A system and image detector controller 36, which receives commands from the user via an operator interface panel 38, including a prep switch 39 and an exposure switch 41, governs the overall operation of the X-ray apparatus 14. A light 43 is illuminated during various modes of operation as will be described later.

The image photo detector array 26 consists of amorphous silicon devices on a glass substrate. A portion of the light from the scintillator 24 is transmitted through these silicon devices and through the spaces between them. In addition, some of the X-rays are transmitted through both the scintillator 24 and the image photo detector array 26. The output signal from array 26 also is coupled to an exposure control circuit (not shown) that is described in FIGS. 2-4.

Generally the imaging system utilizes a Preshot image from digital detector 26. The Preshot image is obtained from a small dose of X-rays occurring before the X-ray exposure that results in an image of a patient. The number, location and size of the regions of interest (ROIs) on the Preshot image, are used for exposure control, and are defined based on a prescribed Anatomy/View or are automatically calculated from the image data created in detector 26. A typical anatomy view is a chest view. Thus, the AEC field of view can be adjusted for different imaging procedures by selectively combining the signal from one or more ROIs of desired shape and size.

After Prepare switch 39 is pressed, the system defines the Preshot parameters based on the following parameters prescribed by a user of the system: Anatomy/View, Customer Dose selection and Patient size. Patient size generally is limited to small, medium or large. The user enters the parameters from operator interface 38. The Preshot parameters include the X-ray exposure technique, the detector timing, and the synchronization between these two. The X-ray exposure technique includes KV, ma, Mas and many other parameters known to X-ray technicians. The detector timing includes offset timing and readout time. Through interface 38, a user enters all of the Preshot parameters.

After Expose switch 41 is pressed, the system performs the following actions generating an Offset image; Acquiring a Preshot image; Calculation of optimal X-ray dosage, for example, by adjusting exposure time; and Generating an exposure or Final image based on calculated optimal X-ray dosage.

While described with reference to X-ray images other production system such as Magnetic Resonance Imagining, Computed Tomography imaging, Ultrasound Imaging, or other known imaging systems can be used without departing from the spirit of the invention. While the system 100 is not limited to any particular modality, for sake of clarity a simplified an X-ray system has been described.

Methods of an Embodiment

In the previous section, a system level overview of the operation of an embodiment was described. In this section, the particular methods performed by the clients of such an embodiment are described by reference to a series of flowcharts. Describing the methods by reference to a flowchart enables one skilled in the art to develop such programs, firmware, or hardware, including such instructions to carry out the methods on suitable computerized clients or the processor of the clients executing the instructions from computer-readable media. Similarly, the methods performed by the server computer programs, firmware, or hardware are also composed of computer-executable instructions. Methods 300 and 700 are performed by a client program executing on, or performed by firmware or hardware that is a part of, a computer, such as computer 202 in FIG. 2, and is inclusive of the acts required to be taken by the processor 204.

Figure 3:
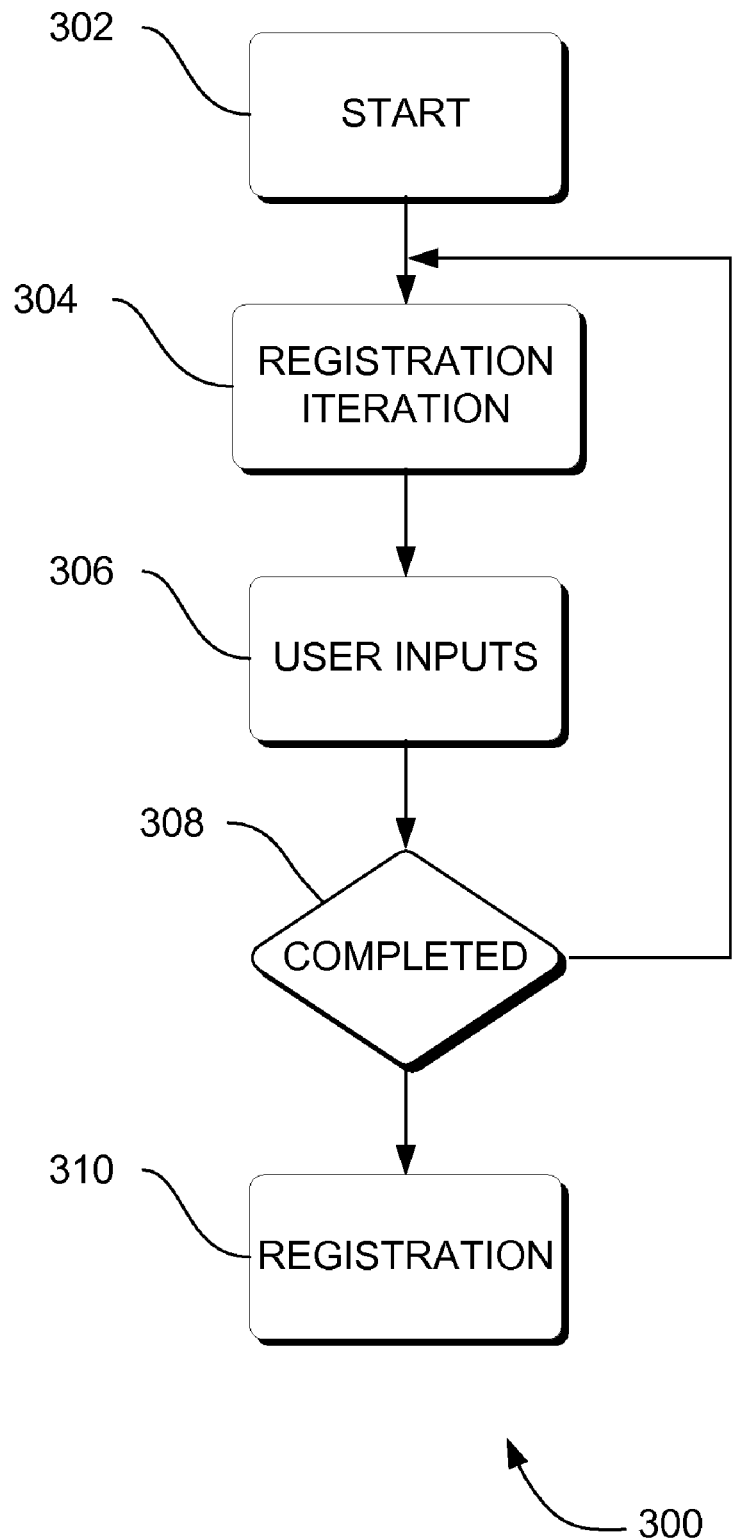
FIG. 3 is a flowchart of a method performed by a client according to an embodiment.

FIG. 3 is a flowchart of a method 300 performed by a client according to an embodiment. Method 300 solves the need in the art for an automatic registration method that overcomes the shortcomings of the prior art.

Method 300 begins with action 302 which starts the registration process. In action 302 all the necessary modules, components, or subroutines with all necessary images are loaded into working storage (RAM) so as to be manipulated by the automatic registration process. All data gathered from multiple scans of a patient is to be considered one data set. Each data set can be broken up into smaller units, either pixels or voxels. When the data set is two-dimensional, the image is made up of units called pixels. A pixel is a point in two-dimensional space that can be referenced using two dimensional coordinates, usually x and y. Each pixel in an image is surrounded by eight other pixels, the nine pixels forming a three-by-three square. These eight other pixels, which surround the center pixel, are considered the eight-connected neighbors of the center pixel. When the data set is three-dimensional, the image is displayed in units called voxels. A voxel is a point in three-dimensional space that can be referenced using three-dimensional coordinates, usually x, y and z. Each voxel is surrounded by twenty-six other voxels. These twenty-six voxels can be considered the twenty-six connected neighbors of the original voxel. Generally, three-dimensional magnetic brain images have been segmented by connectivity; however, there are usually connections between the intracranial volume and the scalp. One path that connects the brain to the scalp is along the optic nerve to the fluid filled eye globes and then the facial tissue. One or more seeds in placed in the object and wavelets data structure representing the voxels contained within a sphere of a fixed spherical radius. After action 302 control passes to action 304 for further processing.

Action 304 performs registration iteration. In registration iteration 304 the images are smoothed with a Gaussian shaped kernal followed by down-sampling. The procedure for registration iteration a three-dimensional medical images containing an object of interest comprises generating a plurality of successive layers of fixed radius spheres about a circumference of a sphere containing at least one seed point placed within the object of interest when a plurality of respective voxels contained within the spheres exceed a selected threshold. The procedure repeats the generation of layers until no further voxels contained within an outer surface of each respective layer exceed a selected threshold, the layers forming a segmented representation of the object of interest. The radius is selected in accordance with a desired radius of curvature of the segmented representation. Further layers of spheres within a segmented representation of the object is wholly contained within the object of interest. The computed set of levels can then be used by the processor to speed up the processing. Once the images have been processed control passes to action 306 for further processing.

In action 306, a user inputs is received. In action 306 the user can offer assistance via a graphical user interface (GUI). The user's assistance can represent algorithm parameters such as translation, rotation, and scaling. It should be noted that the calculated levels (action 304) can be used to limit when or how many user inputs would be processed by the processor. For example, user inputs could be held in temporary storage until a given level has been reached or a certain number of iterations have been processed. The user input can take the form of clicking and dragging a pointing device (mouse or stylus) on orthogonal image slices displayed as a 3-D rendering. For example, dragging the left mouse button can translate the image in the direction of motion, and dragging the right mouse button can rotate about the axis normal to the particular image slice. Once the user inputs have been received control passes action 308 for further processing.

In action 308, a completion determination is ascertained. The computed levels in action 304 can be used to determine the point of completion of the registration process. This completion can be based on the number of iterations and number of levels that have been registered. This completion can also be based on detecting algorithm convergence. Repeating these steps several times results in a scale space of several levels. Then, registration begins at the coarsest level of scale space, iterates to convergence at that level, and then proceeds to the next level of higher resolution. The effect is the double benefit of a faster solution, and a solution that is less likely to become trapped in a local minimum. The proposed algorithm is well suited for such multi-scale techniques because the user's input can be incorporated at the current level, and it can speed-up the convergence at that level. User input is most valuable at the coarsest level, where the clinician's recognition capabilities can be exploited to avoid becoming trapped in local minima. Registration at the finest level is best suited for the computer to perform, where sub-voxel fine-tuning is too tedious for humans. If the registration is not completed control is returned to action 304 for further processing. When the registration is completed control passes to action 310.

In action 310 the registration is completed. The completed registration is sent to a display device (222, 32) for presentation to the user or to remote users connected through a suitable network.

Figure 2:
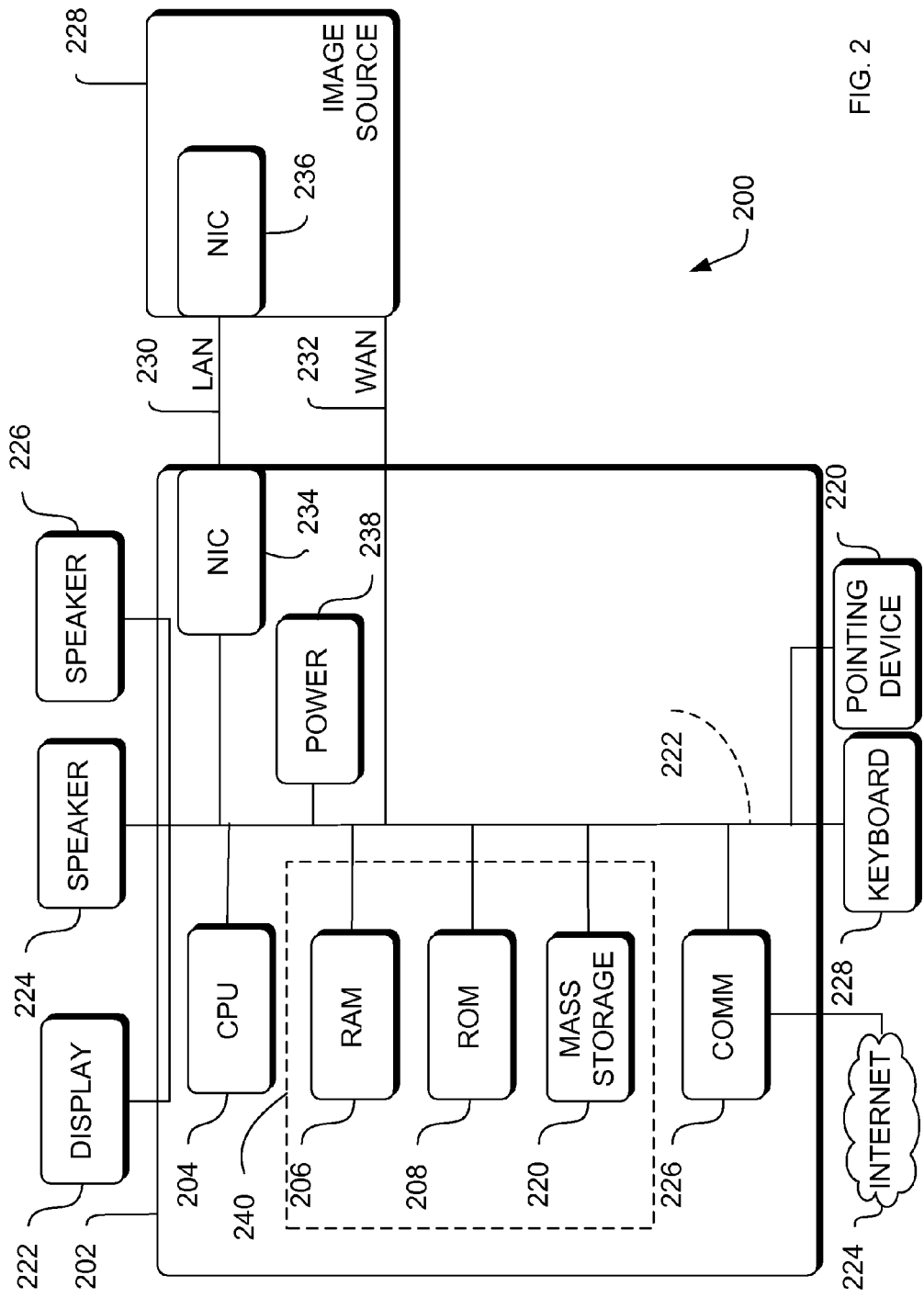
FIG. 2 is a block diagram of the hardware and operating environment in which different embodiments can be practiced.

In some embodiments, method 300 is implemented as a computer data signal embodied in a carrier wave, that represents a sequence of instructions which, when executed by a processor, such as processor 204 in FIG. 2, cause the processor to perform the respective method. In other embodiments, method 300 is implemented as a computer-accessible medium having executable instructions capable of directing a processor, such as processor 204 in FIG. 2, to perform the respective method. In varying embodiments, the medium is a magnetic medium, an electronic medium, or an optical medium.

Figure 4:
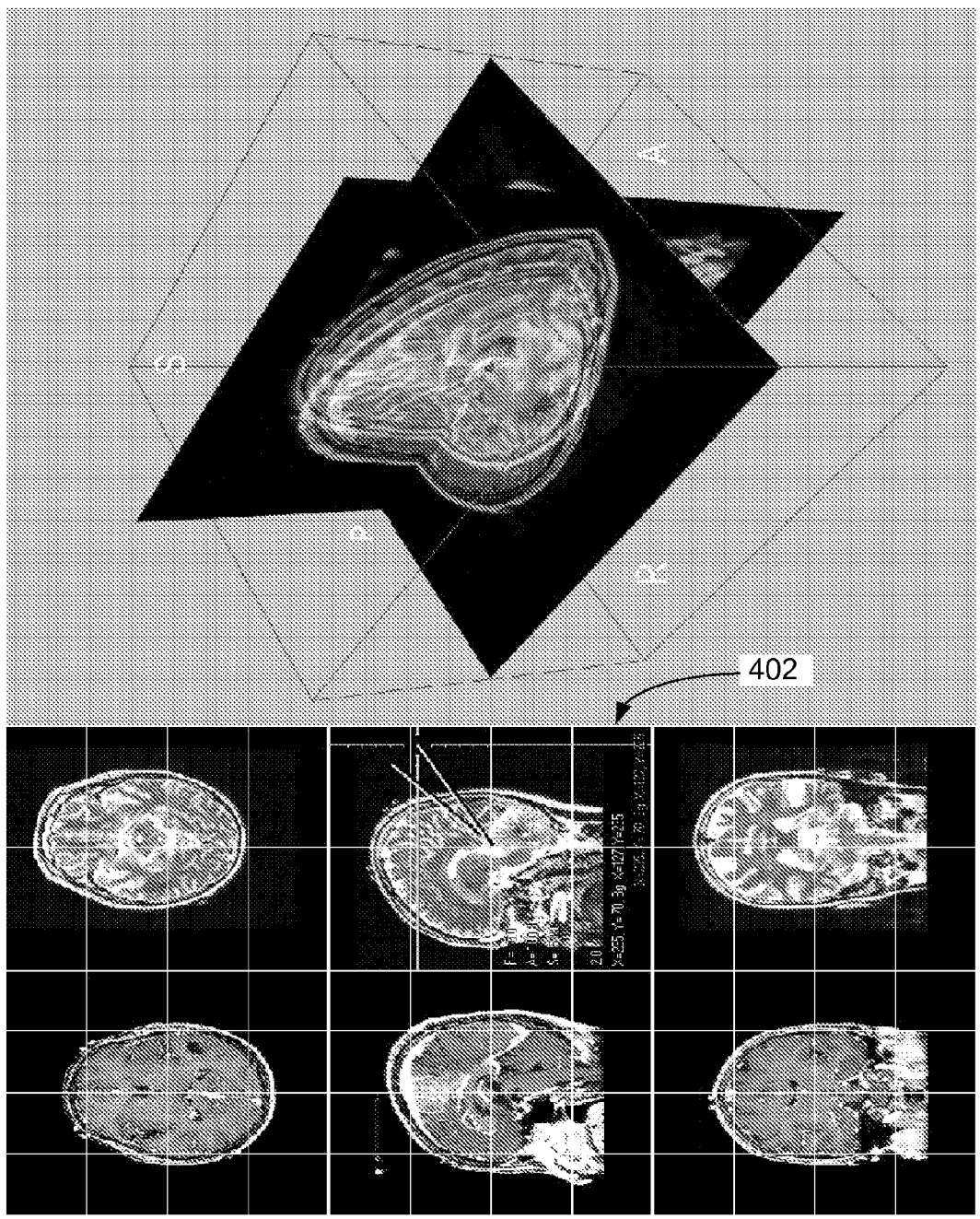
FIG. 4 is a orthogonal image slices displayed as a 3-D rendering with graphical cues drawn on the image while dragging the mouse in accordance to an embodiment.
Figure 5:
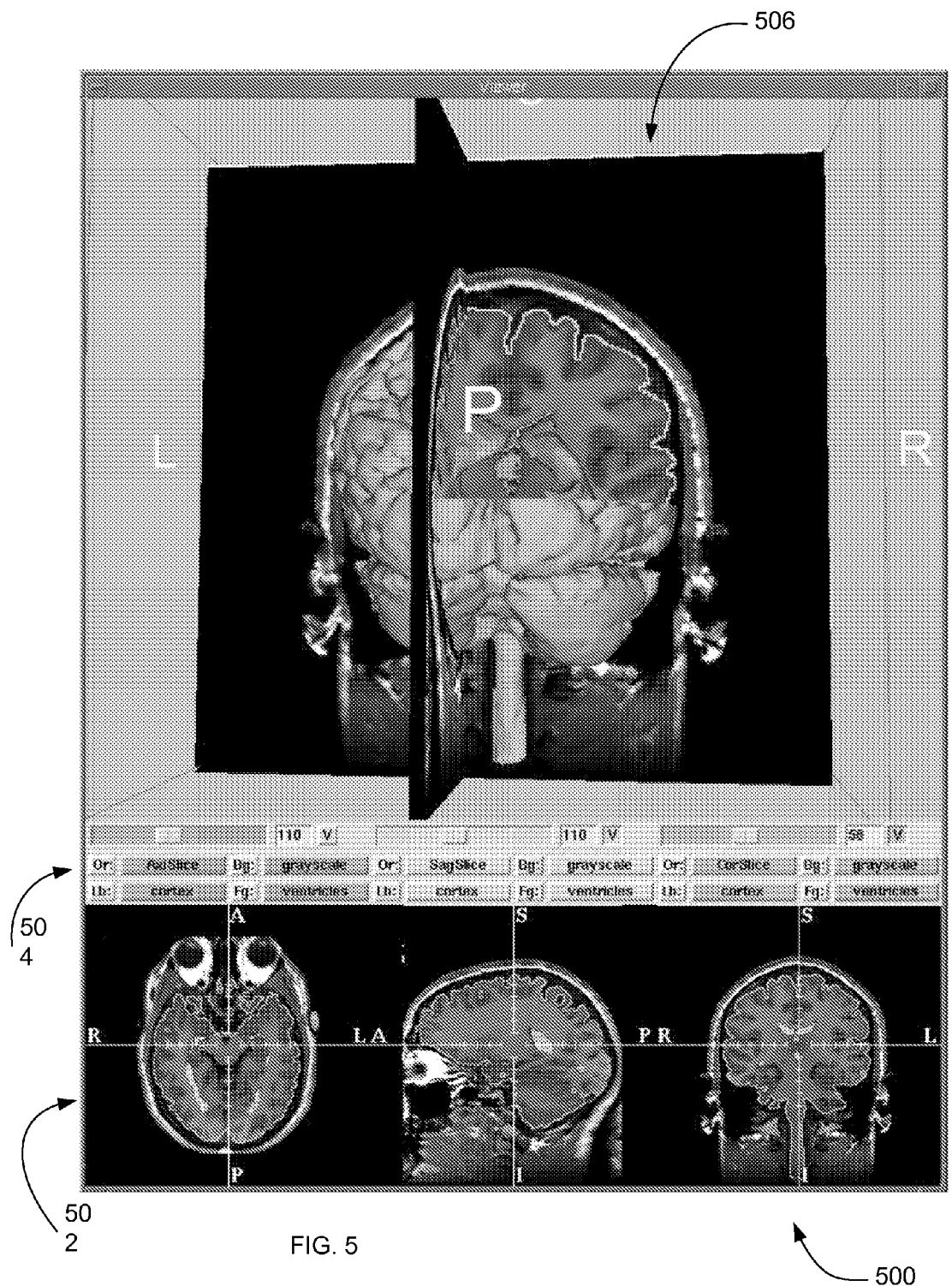
FIG. 5 is a view of a graphical user interface (GUI) according to an embodiment.
Figure 6:
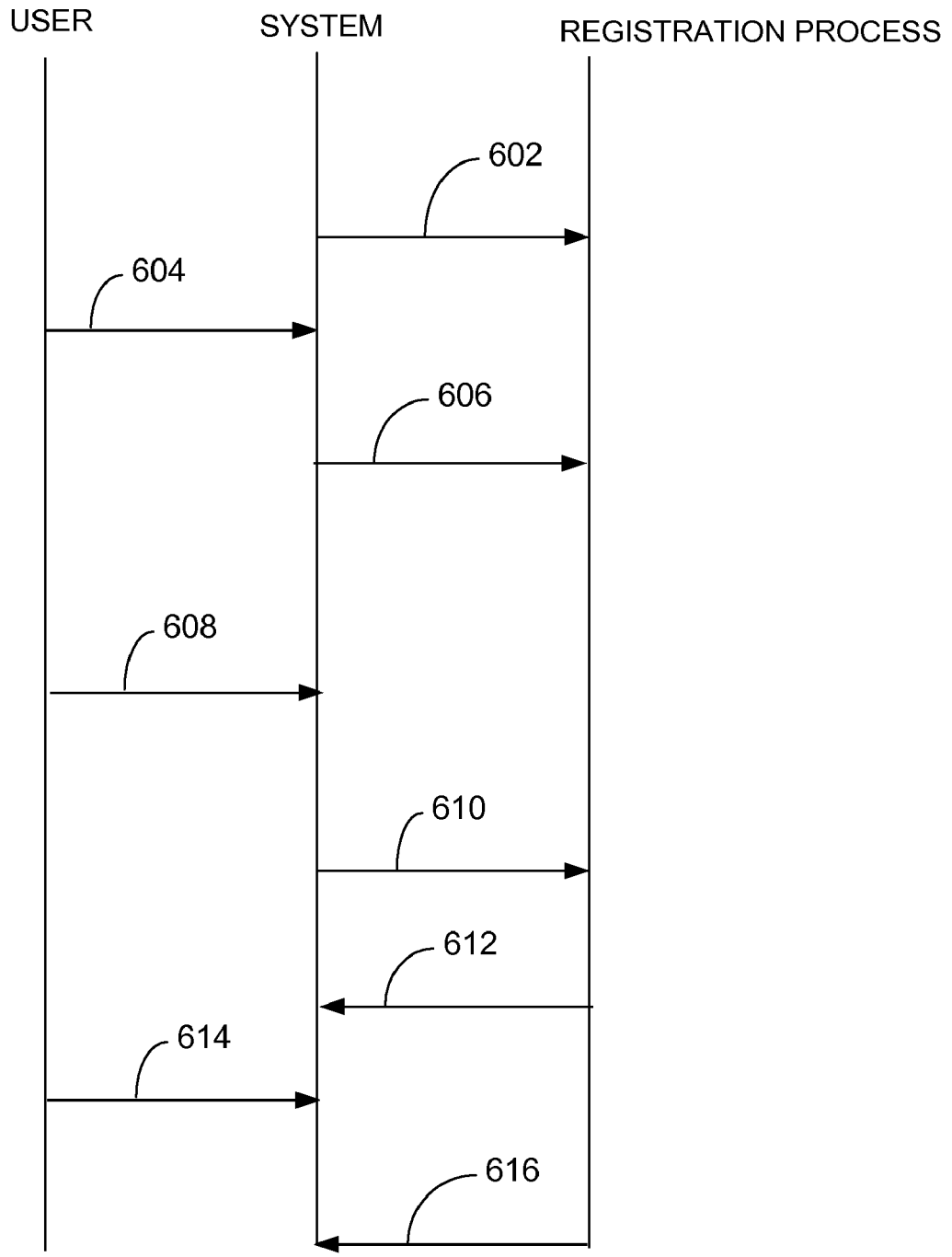
FIG. 6 is an interactive flow diagram illustrating interaction between a user, a system, and a registration process during automatic registration.

Referring to FIGS. 4-6, a particular implementation is described in conjunction with the system overview in FIG. 1 and the methods described in conjunction with FIG. 3. The figures use the Unified Modeling Language (UML), which is the industry-standard language to specify, visualize, construct, and document the object-oriented artifacts of software systems. In the figures, an arrow between classes is used to indicate that a child class below a parent class inherits attributes and methods from the parent class. Composition defines the attributes of an instance of a class as containing an instance of one or more existing instances of other classes in which the composing object does not inherit from the object (s) it is composed of.

The system components can be embodied as computer hardware circuitry or as a computer-readable program, or a combination of both. In another embodiment, the system implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 202 in FIG. 2, or on at least as many computers as there are components.

FIG. 4 shows a display 400 of slices of an operator interface of a of a patient's body, or selected portion of a patient's body and a montage of those slices into a three dimensional representation. Further, notice graphical cues drawn on the image while dragging the mouse at 402. The scan data typically consists of a series of two-dimensional images that represent slices taken through the structure that was the subject of the scan. The two-dimensional images are converted or transformed into a three-dimensional image as shown. The two-dimensional images may be typically obtained from a helical CT scanner operated by a computer console. For example, the scanner may be a General Electric Helical CT Scanner connected with an optional General Electric Independent computer console or physician's console. The computer console may, however, be an integral part of the helical CT scanner instead of a separate independent console. The two-dimensional images can also be obtained from ultrasound, positron emission tomography, emission computed tomography, and magnetic resonance imaging. The physical property measured is directly associated with the scanning technique used to produce the two-dimensional images. For CT images the physical property measured is typically X-ray attenuation, while for magnetic resonance images (MRI) the physical property measured is generally related to various properties such as proton density.

FIG. 5 shows a graphical user interface (GUI) 500 in accordance to an aspect of the invention. The GUI as shown consist of a slice pane 502, an image information pane 504, and a three-dimensional representation pane. The output of segmentation is displayed with variable opacity over the original grayscale images. The three slices on the bottom of the screen correspond to those shown above in the three-dimensional view.

FIG. 6 shows the interaction between the system, the registration process, and the user. Action 602 begins the process with the system sending imaging data or a dataset consisting of modified imaging data to the registration process. While the registration process is operating on the received data the user in action 604 can suggest changes. The changes can be acquired either through poling or through well placed interrupts. During rigid or affine registration, assistance can be offered by the user via GUI (Graphical User Interface) 500 controls such as sliders. The controls represent the algorithm parameters, such as translation, rotation, and scaling. More conveniently, user input can take the form of clicking and dragging a pointing device (e.g.: mouse or stylus) on orthogonal image slices displayed as a montage, or a 3-D rendering, or both, as shown in the figure below. For example, dragging the left mouse button can translate the image in the direction of motion, and dragging the right mouse button can rotate about the axis normal to the particular image slice.

During non-rigid registration or warping, user input can be entered in the same manner, but the impact is felt locally rather than globally. For example, warping is usually represented by a flow field, which is a set of vectors, one per image voxel. Dragging the pointing device on an image slice could contribute strongly to the flow vectors within the immediate vicinity of the click, and with decreasing magnitude with increasing distance. That is, the effect is applied locally and smoothed into the surrounding flow field. The scope of this smoothing could be indicated by the user. For example, a Region Of Interest (ROI) where the effect is to be felt the strongest could be indicated by drawing a polygon with the right mouse button, and then the input vector's direction and magnitude could be indicated by following this motion with a dragging of the left mouse button.

The user's changes 604 can be incorporated by the system to help the algorithm achieve a quicker and more reliable solution. The means of incorporating the user's input into the registration algorithm is especially straightforward for iterative methods, such as when the method for searching the space of allowable transformations is stochastic gradient descent. With this method, the algorithm makes several thousand iterations of computing the image gradient and refining the set of translations and rotations (pose). The gradient is computed stochastically because it is computed only for a small random sample of image voxels such as 50 samples from a 3-D image with 8-million voxels. In this manner, the prototype registers the T1-weighted and T2-weighted images shown in FIG. 4. Using a similarity metric of correlation instead of mutual information, useful for registering T1-weighted to T1-weighted images, the processing time is between a ¼ to a ⅓ long. In this framework where there are many stochastic iterations to update a pose, the user's input can be incorporated by adjusting the pose between iterations thus making it jump closer toward the desired solution.

To speed up the processing, registration is often performed at several levels of resolution. The set of levels are computed by smoothing the original image with a Gaussian shaped kernel, followed by down-sampling. Repeating these steps several times results in a scale space of several levels. Then, registration begins at the coarsest level of scale space 602, iterates to convergence at that level, and then proceeds to the next level of higher resolution 606. The effect is the double benefit of a faster solution, and a solution that is less likely to become trapped in a local minimum. The proposed multi-scale techniques the user's input (604, 608, 614) can be incorporated at the current level and it can speed-up the convergence at that level (602, 606, 610). User input is most valuable at the coarsest level, where the clinician's recognition capabilities can be exploited to avoid becoming trapped in local minima. Registration at the finest level is best suited for the computer to perform, where sub-voxel fine-tuning is too tedious for humans. As shown in the timing sequence 600 instances where the user input 614 is of little value is not communicated to the registration process.

Figure 7:
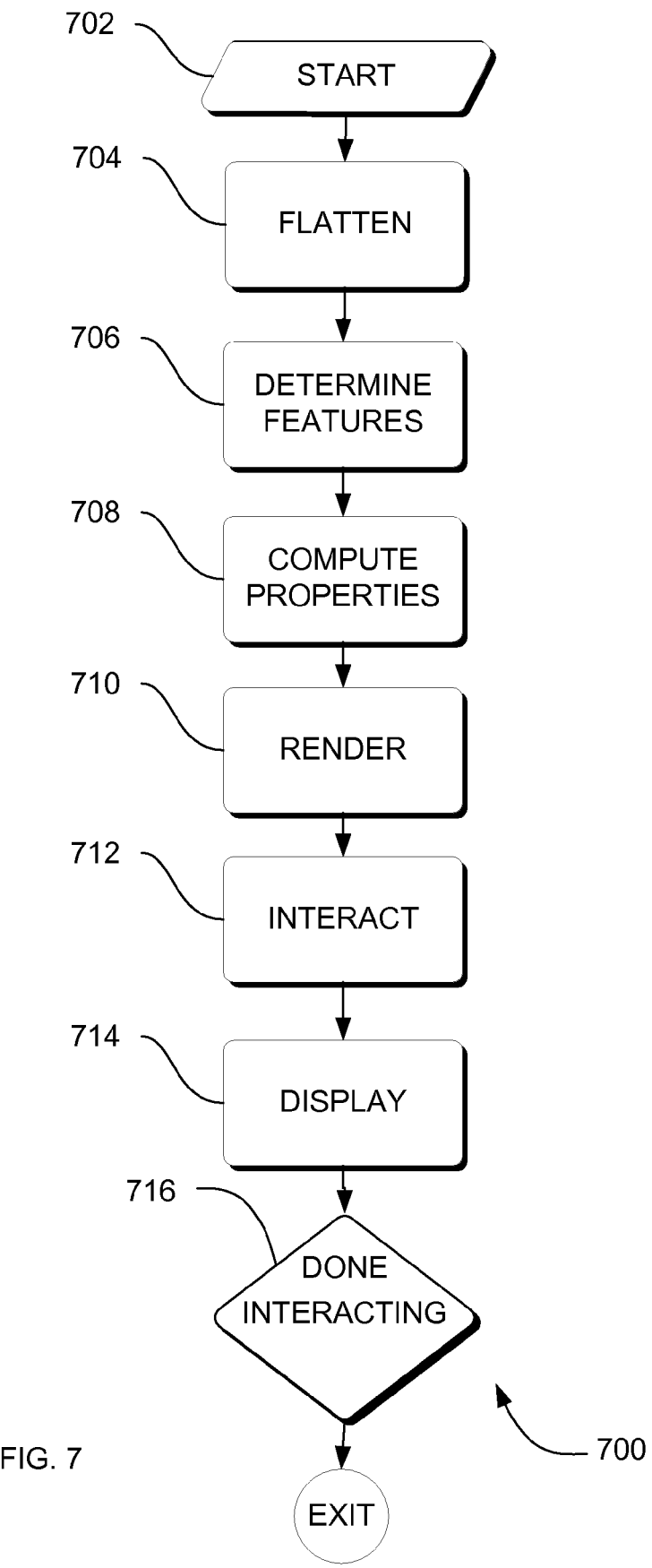
FIG. 7 is a flowchart of a method performed by a client according to an embodiment.

FIG. 7 is a flowchart of a method 700 performed by a client according to an embodiment. Method 700 solves need in the art for a system and method for interacting with an anatomical surface.

Method 700 begins with action 702. Action 702 starts the process at the moment that its instantiated by either the system, a user, or a process. Action 702 can include the accessing of three dimensional anatomical surface, the accessing of images that can be consolidated to form a three dimensional anatomical surface, and the accessing of all data needed by method 700 to allow interaction of images by a user or system. The accessing of data can be from temporary storage, permanent storage, or information received through a network such as the internet. After, the process has been started and information has been acquired control passes to action 704 for further processing.

In action 704, the accessed information is flattened to make it easier for interacting. The flattening process could be accomplished in one of two ways. The first method involves projecting the anatomical surface toward a simpler geometric shape. The choice of the simple geometric shape depends on the general shape of the anatomy. For example, the shape could be a plane, cylinder, or sphere. A method for mapping the surface to a plane will be described below for the clinical example of a physis (growth plate). In another example, the mapping of the surface of the colon to a cylinder to facilitate virtual colonoscopy can be found in A. V. Bartroli, R. Wegenkittl, A. Konig, E. Groller, E. Sorantin, Virtual Colon Flattening, VisSym (2001) pages 127-136, and the mapping of the surface of the cortex to a sphere can be found in S. Haker, S. Angenent, A. Tannenbaum, R. Kikinis, G. Sapiro, M. Halle, Conformal Surface Parameterization for Texture Mapping, IEEE Transactions on Visualization and Computer Graphics April-June 2000. The second method treats the problem of reducing three dimensional (3-D) data to two dimensional (2-D) data as an instance of the more general problem of data dimensionality reduction. Two examples of mathematical methods for reducing the dimensionality of any arbitrary data set are Isomap and Locally Linear Embedding (LLE).

Figure 8:
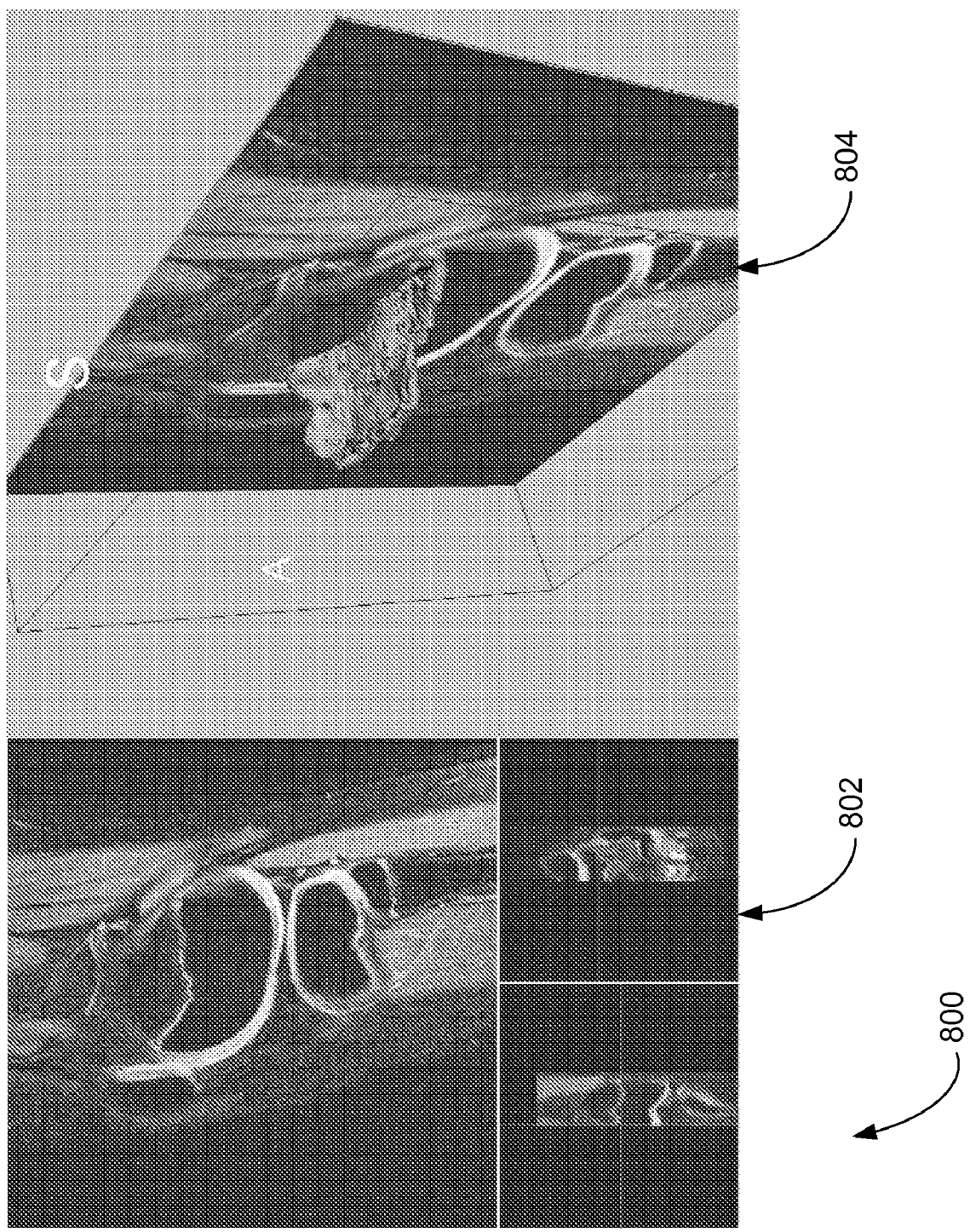
FIG. 8 is a screen shot of the physics segmentation according to an embodiment.
Figure 9:
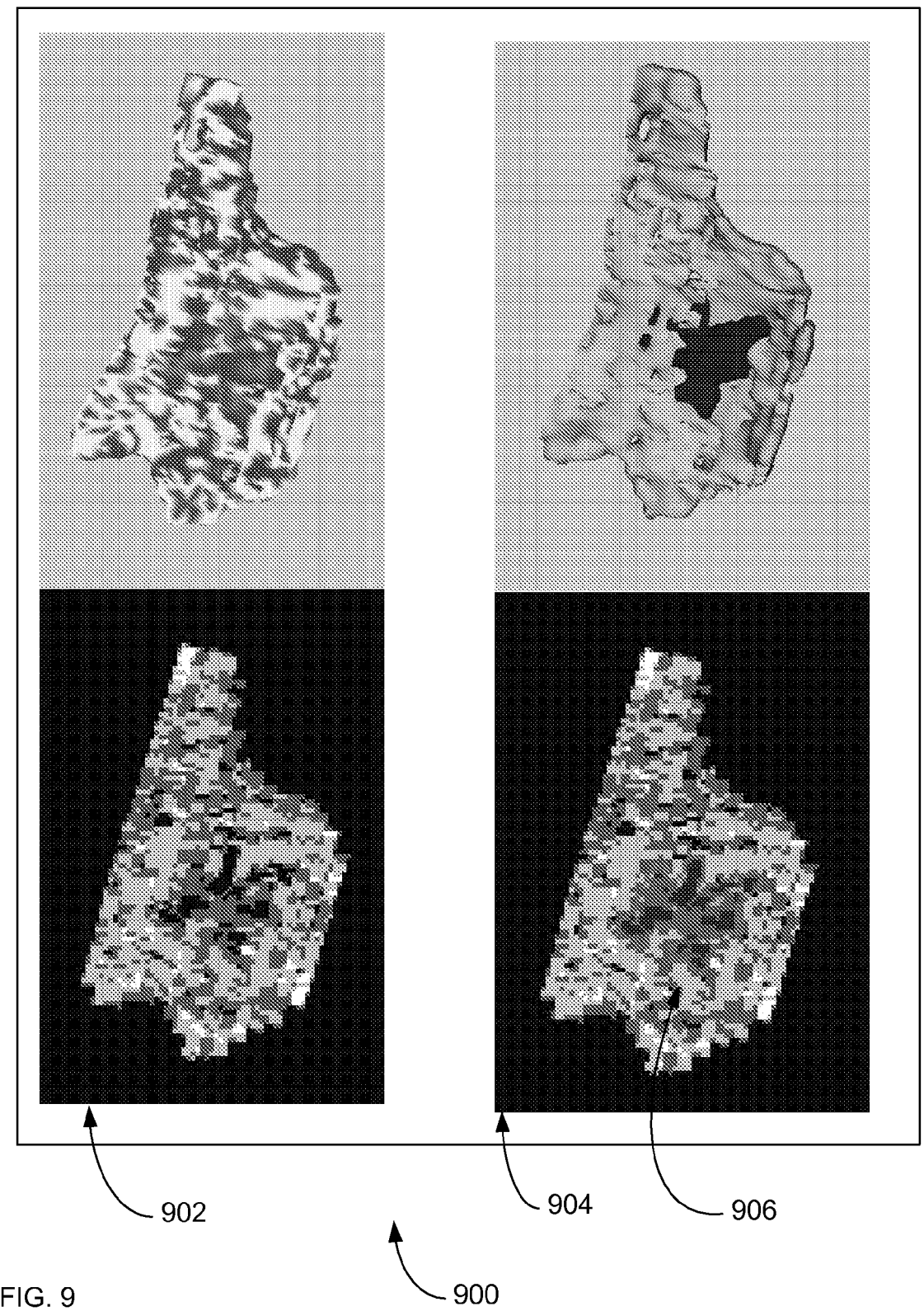
FIG. 9 is a screen shot of a flattened surface with augmentation and user interaction according to an embodiment.

Additionally, besides flattening in order to derive a 2-D image on which to draw, the flattened image can also be augmented to better inform the user regarding where to draw. Properties computed from the 3-D surface, such as thickness and curvature, can be rendered on the flat image. As an example of augmenting the image with thickness, consider the clinical case of segmenting the growing part of a bone (physis) as shown in FIG. 8. In FIG. 9, vertical tile 902 shows a flattened surface augmented with thickness measurements. The lower part of tile 902 shows a two dimensional image of a flattened physis where the intensity of the gray scale voxels is determined by thickness through each point of the plane. The upper part of tile 902 shows a three dimensional (3-D) rendering of the surface color-coded according to thickness.

Figure 10:
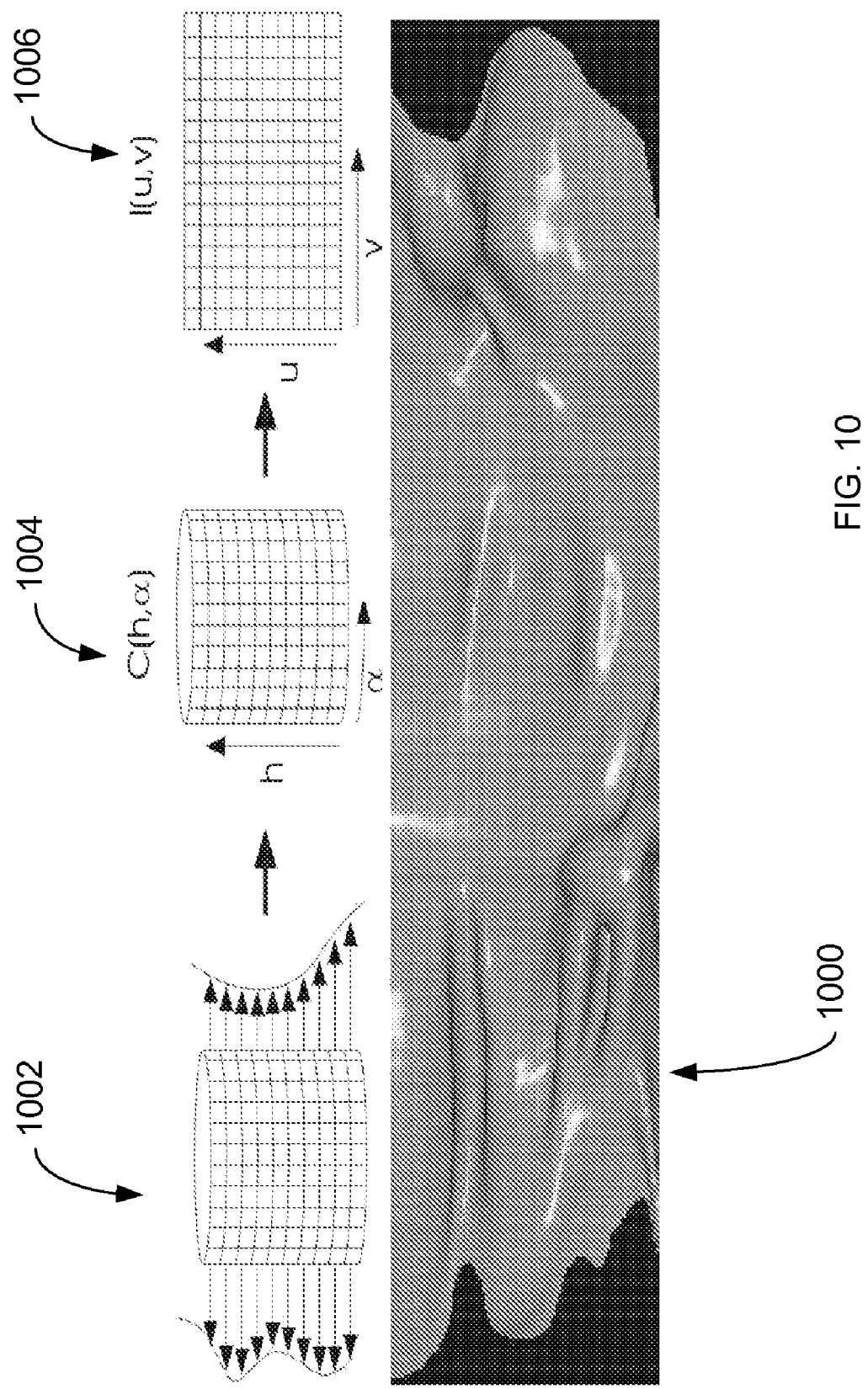
FIG. 10 is an illustration of flattening through projection in accordance to an embodiment.

The process of mapping the physis to a plane involved computing a Principle Component Analysis (PCA) of all the 3-D points identified by the segmentation. See R. O. Duda, P. E. Hart, D. G. Stork, Pattern Classification, John Wiley & Sons, 2001. PCA process rotates the coordinate frame so that the axes are ordered by their usefulness for describing the data. PCA approximates the collection of points by an ellipsoid, and considers the axes of the ellipsoid as the axes of a new, transformed, space. The approximating ellipsoid has a long axis stretching from one cluster to the other: it is this line that defines the new space. For example, FIG. 8 illustrates screenshot of physis segmentation 800. The orthogonal slice planes 802 shows segmentation representing the growing part of a bone (physis). The three dimensional (3-D) surface of physis is shown on 804 projecting outward from the plane. The surface while non-linear could be mapped to a plane. In this physis example, the third and last axis is normal to the plane that best fits the segmentation, and the first two axes lie within this plane. The 3-D image 804 can then be reformatted using the new coordinate frame. The approximate thickness of the physis can then be computed by simply counting the number of voxels along the axis corresponding to thickness. Just as the physis is an anatomical structure that is well suited for mapping to a plane, the articular cartilage is well suited for mapping to a cylinder. The articular cartilage surface could conform to the surface of a virtual cylinder, which could then be flattened simply by unrolling the cylinder's side. FIG. 10 illustrates this process where a region of the surface 1002 is projected to the cylinder 1004 with axes labeled by height and angle. The projection can be computed by casting rays from the cylinder's central axis outward through the cylinder's surface, until contact is made with the segmented surface. The rays can be spaced either at equal angles, or at equal distances along the surface's perimeter. The cylinder is mapped to a two dimensional surface 1006. The bottom tile 1000 shows a flattened colon surface. See, A. V. Bartroli, R. Wegenkittl, A. Konig, E. Groller, E. Sorantin, Virtual Colon Flattening, VisSym, 2001, pages 127-136.

As an alternative to mapping an anatomical surface to a geometrically simpler surface one can apply general algorithms for data dimensionality reduction. Data dimensionality reduction refers to the process of deriving a set of degrees of freedom that may be adjusted to reproduce much of the variability observed within a training set. Consider a set of input data points of dimensionality, D, that lie on or near a smooth underlying nonlinear manifold of lower dimensionality, d. These methods attempt to discover the underlying structure of nonlinear manifolds in order to map a given data set of high-dimensional points into a surrogate low-dimensional space as shown symbolically by the following equation: $X \epsilon \Re^D \Rightarrow Y \epsilon \Re^d$, d<<D.

The Locally linear Embedding (LLE) and Isomap methods are unsupervised manifold learning algorithms while PCA is restricted to learning only linear manifolds. The Isomap and LLE methods can be applied to the problem of anatomy flattening by treating it as a case of reducing three dimensions to two dimensions.

Figure 12:
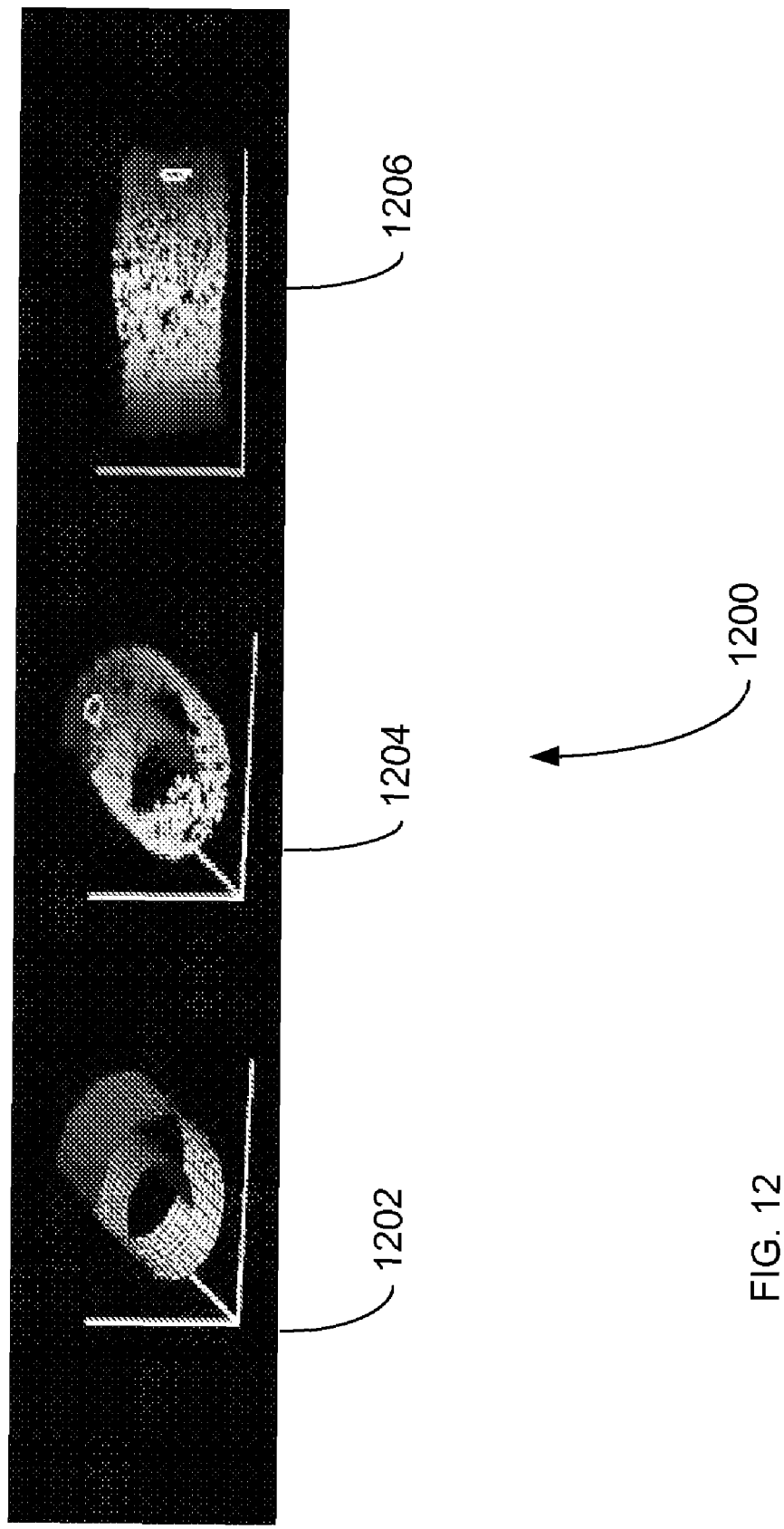
FIG. 12 is an illustration of locally linear embedding (LLE) flattening in accordance to an embodiment.

FIG. 12 shows how an LLE can be applied to a Swiss Roll. The image on the left depicts such a situation where the 3D points form the topology of a 2D rectangular manifold bent into the shape of a 3D S-curve. Imagine using a scissors to cut the manifold into small squares (drawn in white) that represent locally linear patches of the nonlinear S-curve surface. Then position these squares onto a flat tabletop while preserving the angular relationships between neighboring squares. Note that the transplantation is a linear mapping because it involves only the operations of translation, rotation, and scaling of each patch. Thus, the algorithm identifies the data's nonlinear structure through two linear computational steps: first, compute the locally linear patches, and second, compute the linear mapping to a lower dimensional embedding, which is the coordinate system on the manifold.

The main idea behind Locally Linear Embedding (LLE) is to map the input data points to a single global coordinate system of lower dimension in such a way as to preserve the relationships between neighboring points. See, S. T. Roweis, L. K. Saul, Nonlinear Dimensionality Reduction by Locally Linear Embedding, Science December 2000; pages 2323-2326, and Introduction to Locally Linear Embedding. http://www.cs.toronto.edu/~roweis/lle/publications.html. Each data point and its neighbors are expected to lie on, or close to, a locally-linear patch of a manifold. The intrinsic geometry of a patch can be captured by approximating each point by a linear combination of its neighbors. The coefficients for this combination are chosen to be invariant to the transplantation operations such as translation, rotation, and scaling. Therefore, the characterization of local geometry in the original high-dimensional data space will be equally valid in the lower-dimensional space. The algorithm then finds a set of low-dimensional points that can be linearly approximated by their neighbors with the same coefficients that were determined from the high-dimensional data points.

Figure 11:
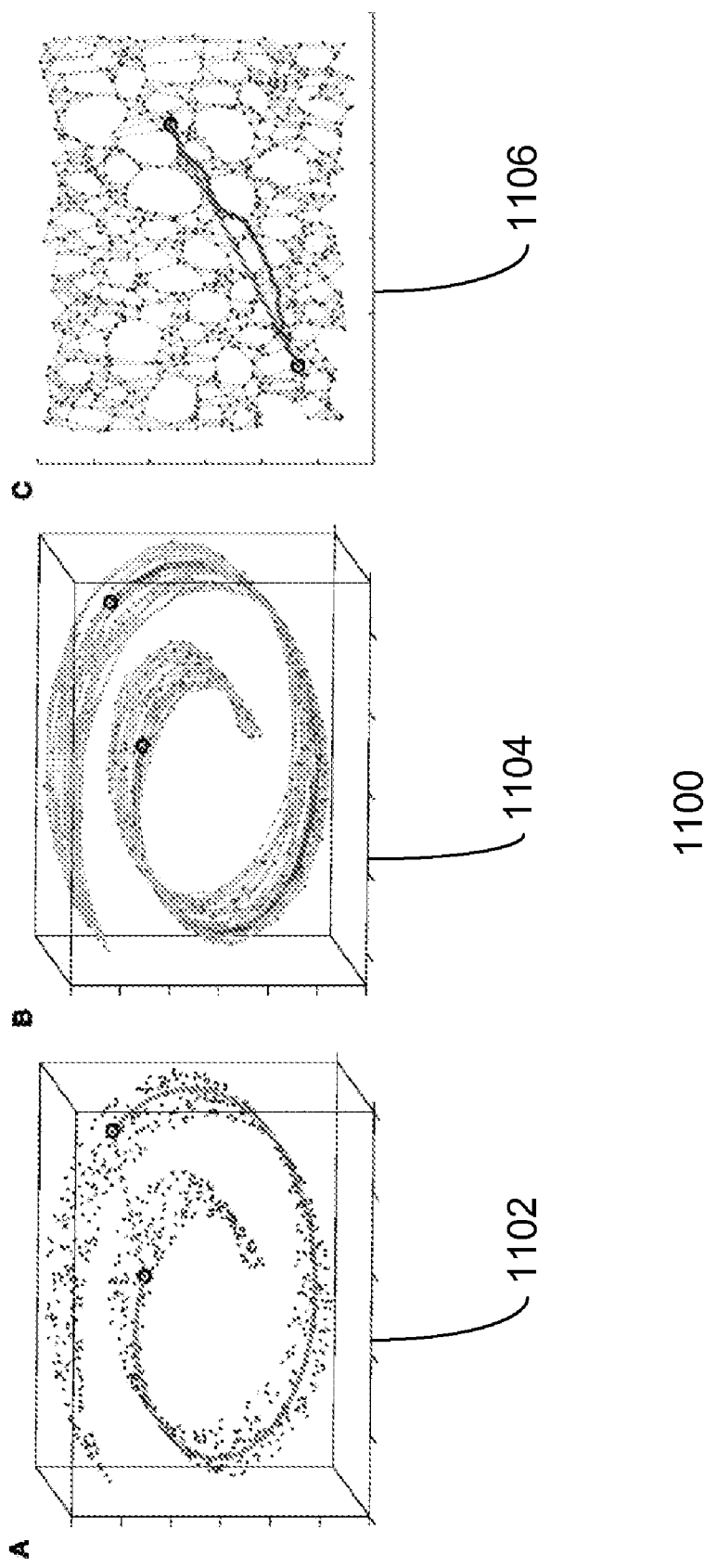
FIG. 11 is an illustration of isomap flattening in accordance to an embodiment.

FIG. 11 shows how Isomap can be applied to a Swiss Roll. The main idea behind the Isomap (isometric feature mapping) algorithm is to perform classical MDS (multi-dimensional scaling) to map data points from their high-dimensional input space to low-dimensional coordinates of a nonlinear manifold. The MDS pair-wise distances are computed not in the input Euclidean space, but in the geodesic space of the manifold. The geodesic distances represent the shortest paths along the curved surface of the manifold (measured as if the surface were flat). Clues to the shape of the manifold are only provided by the input data as surface samples. The actual geodesic distances are therefore approximated by a sequence of short hops between neighboring sample points. Finally, MDS is applied to the geodesic distances to find a set of low-dimensional points with similar pairwise distances. Since only the geodesic distances represent the true, low-dimensional geometry of the manifold, the algorithm is capable of discovering nonlinear degrees of freedom that underlie complex natural observations. The image on the left shows the inaccuracy of Euclidean distance (dashed line) compared with geodesic distance (solid line). The images on the center and right show how the approximation of geodesic distance (red line) overestimates actual distance.

FIG. 12 shows how an Isomap operates on a swiss roll. Inaccuracy of euclidean distance as shown in 1102 by a dashed line compared with geodesic distance as shown by a solid line in 1104. As shown in 1106 approximation of geodesic distance (curved line) overestimates actual distance (straight line). The main idea behind the Isomap or isometric feature mapping algorithm is to perform classical multi-dimensional scaling (MDS) to map data points from their high-dimensional input space to low-dimensional coordinates of a nonlinear manifold. C. Chatfield, A. J. Collins, Introduction to Multivariate Analysis, Chapman & Hall, 1980, and J. B. Tenenbaum, V. d. Silva, J. C. Langford, A Global Geometric Framework for Nonlinear Dimensionality Reduction, Science December 2000, pages 2319-2323, and Introduction to Locally Linear Embedding, http://isomap.stanford.edu/. An important insight is to compute the MDS pair-wise distances not in the input Euclidean space, but in the geodesic space of the manifold. The geodesic distances, measured as if the surface were flat, represent the shortest paths along the curved surface of a manifold. Clues to the shape of the manifold are only provided by the input data as surface samples. The actual geodesic distances are therefore approximated by a sequence of short hops between neighboring sample points. Finally, MDS is applied to the geodesic distances to find a set of low-dimensional points with similar pair-wise distances. Since only the geodesic distances represent the true, low-dimensional geometry of the manifold, the algorithm is capable of discovering nonlinear degrees of freedom that underlie complex natural observations.

Once the three dimensional representation of an anatomical surface has been flattened or transformed to produce a two dimensional representation of anatomical process control is passed to actions 706 and 708 to determine features and properties. These actions are critical to a better understanding and a better interaction with an anatomical surface by a user. As a consequence users are allowed to interact with an augmented display that combines the richness of three dimensional data with the simplicity of two dimensional data. The flattened two dimensional (2-D) surface may be drawn upon for the purposes of performing segmentation, quantitative measurements, or surgical planning. The flattened two dimensional surface is much more convenient to draw upon than a 3-D surface. The flattened two dimensional image being drawn upon can be augmented with properties computed from a 3-D surface. Such an arrangement satisfies the need in the art to perform flattening for the purpose of providing the user with a surface on which to interactively draw easily and accurately.

The flattening process introduces surface deformation. It is mathematically difficult, if the two surfaces do not have the same Gaussian curvature, to perform a mapping between two surfaces that preserves both the angles and area. However, flattening the surface facilitates the computation of some surface properties. For example, if the mapping is thickness-preserving or at least so within acceptable bounds, then the thickness mapping can be performed in the flattened space. Even if not preserved, properties that are easy to compute in the flattened space can be applied in the original space. For example, Locally Linear Embedding (LLE) and Isomap are not thickness-preserving mappings. However, the flattened space could be used to define the surface normal to the flat plane at every point because it is trivial. Then the normal vectors could be mapped back to 3-D space, and then thickness could be measured in 3-D space oriented along the transformed normal vectors. The flattened space could be utilized to easily define the two opposing surfaces between which to measure thickness. Then the thickness measurement could be performed using existing methods such as Iterated Closest Point (ICP) or Partial Differential Equations (PDE). See, A. J. Yezzi, J. L. Prince, A PDE Approach for Measuring Tissue Thickness, Computer Vision and Pattern Recognition (CVPR), Kauai (Hi.), 1998, pages 87-92.

Once the feature and properties are computed in actions 706 and 708 control passes to action 710 for further processing.

In Action 708 a rendering is performed by system 100 or system 200. The action of rendering is inclusive of rendering engines, rendering devices, or display devices that posses or can be coupled to rendering engine for presenting data to a user. A rendering engine is device that produces stream of data consisting of one or more video, graphics, or other media for reproduction at computer 202. The stream of data can be referred to as input data, as an input data stream, as mixed media data, and as mixed media data stream without departing from the original concept of having data be one or more video, graphics, text, animation, or any other data or information produced by a computer. The stream of data can be partitioned at computer 202 to be displayed in sections of the display or by other devices that reproduce the data such as audio, video, or text reproducing devices. The rendering engine can be used in higher resolution medical imaging, in volume rendering of computed tomography (CT) and magnetic resonance imaging (MRI), in 3D visualization that permits rotation and scaling, or for any other purpose that aides in the understating of the physical world.

As noted with reference to FIG. 2 the user station or computer 200 includes any suitable image rendering system or application that can process digital image data of an acquired image dataset 228 or a subset of the dataset to generate and display 2D and 3D images on the display 222. More specifically, the image rendering system may be an application that provides 2D and 3D rendering and visualization of medical image data, and which executes on a general purpose or specific computer workstation. Moreover, the image rendering system enables a user to navigate through a 3D image or a plurality of 2D image slices. The workstation 200 may also include an image rendering system or application for processing digital image data of an acquired image dataset to generate and display 2D and 3D images. As shown in FIG. 2, the visualization module 222 may also be used by the computer 222 to receive and process digital medical image data, which as noted above, may be in the form of raw image data, flattened data or 3D reconstructed data such as volumetric image data or multiplanar formats, or any combination of such formats. The data processing results can be output from the workstation 200 via network 224 to an image rendering system in a remote location for generating 2D and 3D renderings of image data in accordance with the data processing results, such as segmentation of organs or anatomical structures, color or intensity variations, augmentation, and so forth.

The display 222 based on the application can posses frame buffering and compression techniques to augment the displaying and receiving of imaging data. The Frame buffer holds the data stream until it can be displayed. Each address of the frame buffer corresponds to a pixel on the display terminal 222. In this way the frame buffer is a representation of the surface of the display and a cluster of pixels that forms an image or segment of the display can be represented as a collection of addresses on the frame buffer. Frame buffer, constituted of a writable semiconductor memory (SDRAM (Synchronous Dynamic Random Access Memory), for example), a DRAM (Dynamic Random Access Memory), a Rambus DRAM or the like and writes and stores a mixed media data per screen (frame) transferred via a data bus from decompression engine. FIGS. 8, 9, and 10 are renderings of anatomical surfaces. FIG. 9, in particular tile 902, is a rendering of a flattened surface augmented with thickness measurements. Once the flattened surface has been rendered control passes to action 712 for further processing.

In action 712, interaction is performed. With the flattened surface the user could draw on it more easily and more accurately. Further the user could interact with a virtual surface or an augmented surface. That is, instead of rendering just the flattened surface as the 2-D image on which to draw, the rendering could be a map of surface properties, such as thickness or curvature. The user can interact with the flattened surface by drawing a pattern. The pattern could be a shape having a regular or irregular shape. Further, the drawing could be a label, a collection of indices, and representations for a defined path suitable for navigating. Once the user has interacted with the flattened image control passes to action 714 for further processing.

In action 714, the interacted image is displayed. FIG. 9 illustrates a flattened image 904 that has been interacted 906 by a user. The drawing by the user is shown at 906 where the drawn region to segment the physeal region bar for surgical planning. The drawn region (upper part of tile 904) is rendered in three dimensions with measurements concerning diameter, area, volume, and percent of coverage.

Hardware and Operating Environment

FIG. 2 is a block diagram of the hardware and operating environment 200 in which different embodiments can be practiced. The description of FIG. 2 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 202 includes a processor 204, commercially available from Intel, Motorola, Cyrix and others. Computer 202 also includes random-access memory (RAM) 206, read-only memory (ROM) 208, and one or more mass storage devices 210, and a system bus 212, that operatively couples various system components to the processing unit 204. The memory 206, 208, and mass storage devices, 210, are types of computer-accessible media 240. Mass storage devices 210 are more specifically types of nonvolatile computer-accessible media and can include one or more hard disk drives, floppy disk drives, optical disk drives, and tape cartridge drives. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory. The processor 204 executes computer programs stored on the computer-accessible media.

Computer 202 can be communicatively connected to the Internet 214 via a communication device 216. Internet 214 connectivity is well known within the art. In one embodiment, a communication device 216 is a modem that responds to communication drivers to connect to the Internet via what is known in the art as a "dial-up connection." In another embodiment, a communication device 216 is an Ethernet® or similar hardware network card connected to a local-area network (LAN) that itself is connected to the Internet via what is known in the art as a "direct connection" (e.g., T1 line, etc.).

A user enters commands and information into the computer 202 through input devices such as a keyboard 218 or a pointing device 220. The keyboard 218 permits entry of textual information into computer 202, as known within the art, and embodiments are not limited to any particular type of keyboard. Pointing device 220 permits the control of the screen pointer provided by a graphical user interface (GUI) of operating systems such as versions of Microsoft Windows®. Embodiments are not limited to any particular pointing device 220. Such pointing devices include mice, touch pads, trackballs, remote controls and point sticks. Other input devices (not shown) can include a microphone, joystick, game pad, satellite dish, scanner, or the like.

In some embodiments, computer 202 is operatively coupled to a display device 222. Display device 222 is connected to the system bus 212. Display device 222 permits the display of information, including computer, video and other information, for viewing by a user of the computer. Embodiments are not limited to any particular display device 222. Such display devices include cathode ray tube (CRT) displays (monitors), as well as flat panel displays such as liquid crystal displays (LCD's). In addition to a monitor, computers typically include other peripheral input/output devices such as printers (not shown). Speakers 224 and 226 provide audio output of signals. Speakers 224 and 226 are also connected to the system bus 212.

Computer 202 also includes an operating system (not shown) that is stored on the computer-accessible media RAM 206, ROM 208, and mass storage device 210, and is and executed by the processor 204. Examples of operating systems include Microsoft Windows®, Apple MacOS®, Linux®, UNIX®. Examples are not limited to any particular operating system, however, and the construction and use of such operating systems are well known within the art.

Embodiments of computer 202 are not limited to any type of computer 202. In varying embodiments, computer 202 comprises a PC-compatible computer, a MacOS®-compatible computer, a Linux®-compatible computer, or a UNIX®-compatible computer. The construction and operation of such computers are well known within the art.

Computer 202 can be operated using at least one operating system to provide a graphical user interface (GUI) including a user-controllable pointer. Computer 202 can have at least one web browser application program executing within at least one operating system, to permit users of computer 202 to access intranet or Internet world-wide-web pages as addressed by Universal Resource Locator (URL) addresses. Examples of browser application programs include Netscape Navigator® and Microsoft Internet Explorer®.

The computer 202 can operate in a networked environment using logical connections to one or more remote computers, such as remote computer 228. These logical connections are achieved by a communication device coupled to, or a part of, the computer 202. Embodiments are not limited to a particular type of communications device. The image source 228 or remote computer can be another computer, a server, a router, a network PC, an image repository, an imaging device, a client, a peer device or other common network node. The logical connections depicted in FIG. 2 include a local-area network (LAN) 230 and a wide-area network (WAN) 232. Such networking environments are commonplace in offices, enterprise-wide computer networks, intranets and the Internet.

When used in a LAN-networking environment, the computer 202 and remote computer 228 are connected to the local network 230 through network interfaces or adapters 234, which is one type of communications device 216. Remote computer 228 also includes a network device 236. When used in a conventional WAN-networking environment, the computer 202 and remote computer 228 communicate with a WAN 232 through modems (not shown). The modem, which can be internal or external, is connected to the system bus 212. In a networked environment, program modules depicted relative to the computer 202, or portions thereof, can be stored in the remote computer 228.

Computer 202 also includes power supply 238. Each power supply can be a battery.

CONCLUSION

An automatic image registration methodology and an image interacting methodology have been described with reference to systems and methods. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in object-oriented terms, one of ordinary skill in the art will appreciate that implementations can be made in a procedural design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. A general description of image registration and image flattening or flattening with associated algorithms and registration strategies can be found in the following publications that are hereby incorporated by reference:

[Gering00] D. T. Gering, A. Nabavi, R. Kikinis, N. Hata, L. J. O'Donnell, W. E. L. Grimson, F. A. Jolesz, P. M. Black, W. M. Wells. "An integrated visualization system for surgical planning and guidance using image fusion and an open MR". *JMRI* 2000; 13:967-975.

[Press92] W.H. Press, B. P. Flannery, S. A. Teukolsky, W. T. Vetterling. *Numerical Recipes in C: The Art of Scientific Computing*. Cambridge University Press, 1992.

[Slicer] 3D Slicer. http://www.slicer.org.

[Thirion09] T. P. Thirion. "Image matching as a diffusion process: an analogy with Maxwell's demons". *Medical Image Analysis* 1998; 2:

[Viola97] P. Viola, W. M. Wells. "Alignment by maximization of mutual information". *International Journal of Computer Vision* September 1997; 24:137-154.

[Wells96] W. M. Wells, P. Viola, H. Atsumi, S. Nakajima, R. Kikinis. "Multi-modal volume registration by maximization of mutual information". *Medical Image Analysis* 1996;

[Bartroli01] A. V. Bartroli, R. Wegenkittl, A. Konig, E. Groller, E. Sorantin. "Virtual Colon Flattening". In: *VisSym* 2001. 2001; 127-136.

[Chatfield80] C. Chatfield, A. J. Collins. *Introduction to Multivariate Analysis*. Chapman & Hall, 1980.

[Duda01] R. O. Duda, P. E. Hart, D. G. Stork. *Pattern Classification*. John Wiley & Sons, 2001.

[Haker00] S. Haker, S. Angenent, A. Tannenbaum, R. Kikinis, G. Sapiro, M. Halle. "Conformal Surface Parameterization for Texture Mapping". *IEEE Transactions on Visualization and Computer Graphics* April-June 2000; 6:

[Roweis00] S. T. Roweis, L. K. Saul. "Nonlinear Dimensionality Reduction by Locally Linear Embedding". *Science* December 2000; 290:2323-2326.

[Roweis01] Introduction to Locally Linear Embedding. http://www.cs.toronto.edu/~roweis/lle/publications.html.

[Tenenbaum00] J. B. Tenenbaum, V. d. Silva, J. C. Langford. "A Global Geometric Framework for Nonlinear Dimensionality Reduction". *Science* December 2000; 290:2319-2323.

[Tenenbaum01] Introduction to Locally Linear Embedding. http://isomap.stanford.edu/.

[Yezzi01] A. J. Yezzi, J. L. Prince. "A PDE Approach for Measuring Tissue Thickness". In: *Computer Vision and Pattern Recognition (CVPR)*. Kauai, Hi.: 1998; 87-92.

I claim:

1. A computerized method for image registration, the computerized method comprising:
accessing a set of images to be registered through an automatic registration process;
selecting an automatic registration process;
applying the selected automatic registration process on the acquired set of images;
receiving user input;
incorporating the received user input into the current stage of the application of the selected registration process on the acquired set of images; and
repeating the action of receiving and incorporating until the registration of the acquired set of images is within a predetermined condition.

2. The computerized method of claim 1, wherein the acquired set of images further comprises:
one or more MRI image, CT image, pathology image, image with artifacts, X-ray image, ultrasound image, region of interest image.

3. The computerized method of claim 2, wherein the automatic registration process further comprises:
a process of rigid registration, warping registration, a combination of rigid and non-rigid registration, multi-scale registration, localized correlation or localized mutual information registration.

4. The computerized method of claim 3, wherein the user input further comprises:
one or more global control, localized control, pasting.

5. The computerized method of claim 4, further comprising:
applying localized control to a region of a selected image; and
applying pasting to images that are tiled with very little overlap.

6. The computerized method of claim 5, wherein the user input further comprises:
one or more translation factor, rotation factor, scaling factor, region of interest factor, flow vectors.

7. The computerized method of claim 1, the computerized method further comprising:
displaying image registration information;
wherein image registration information is one or more side-by-side comparison, blended overlay, side-by-side comparison and blended overlay, user defined information.

8. The computerized method of claim 1, the computerized method further comprising:
displaying graphical cues from received user inputs.

9. A computer-accessible medium having executable instructions for image registration, the executable instructions capable of directing a processor to perform:
accessing a set of images to be registered through an automatic registration process;
selecting an automatic registration process;
applying the selected automatic registration process on the acquired set of images;
receiving user input;
incorporating the received user input into the current stage of the application of the selected registration process on the acquired set of images; and
repeating the action of receiving and incorporating until the registration of the acquired set of images is within a predetermined condition.

10. The computer-accessible medium of claim 9, wherein the automatic registration process further comprises:
a process of rigid registration, warping registration, a combination of rigid and non-rigid registration.

11. The computer-accessible medium of claim 10, wherein the user input further comprises:
one or more global control, localized control, pasting.

12. The computer-accessible medium of claim 9, wherein the user input further comprises:
one or more translation factor, rotation factor, scaling factor, region of interest factor, flow vectors.

13. A system for image registration between a first image and a second image of an object, the system comprising:
a registration process calculator configured to perform automatic registration;
a graphical user interface configured to receive user input;
wherein the registration process calculator incorporates the received user input into the current stage of the automatic registration; and
wherein the registration process calculator continues to perform automatic registration and to incorporate user input until a target registration error has been computed.

14. The system of claim 13, wherein the automatic registration is one of rigid registration, warping registration, a combination of rigid and non-rigid registration, multi-scale registration, similarity registration, localized correlation or localized mutual information registration.

15. The system of claim 14, wherein the first or second image can be one or more MRI image, CT image, pathology image, image with artifacts, X-ray image, ultrasound image, region of interest image.

16. The system of claim 15, wherein the automatic registration is one of rigid registration, warping registration, a combination of rigid and non-rigid registration, multi-scale registration, similarity registration, localized correlation or localized mutual information registration.

17. The system of claim 13, wherein user input further comprises:
one or more global control, localized control, pasting;
wherein global control is applied to a selected image;
wherein localized control is applied to a region of a selected image; and
wherein pasting is when the user aligns images that are tiled with very little overlap.

18. The system of claim 13, wherein the user input further comprises:
one or more translation factor, rotation factor, scaling factor, region of interest factor, flow vectors.

19. The system of claim 18, the system further comprising:
display device for displaying image registration information;
wherein image registration information is one or more side-by-side comparison, blended overlay, side-by-side comparison and blended overlay, user defined information.

20. The system of claim 18, the system further comprising:
display device for displaying graphical cues from received user inputs.

* * * * *